United States Patent
Danscher

(10) Patent No.: US 7,655,261 B2
(45) Date of Patent: Feb. 2, 2010

(54) MEDICAMENT AND METHOD OF TREATMENT OF PATIENTS WITH HEAVY METALS

(76) Inventor: Gorm Danscher, Gentoftevej 7, Århus C (DK) 8000

( * ) Notice: Subject to any disclaimer, the term of this patent is extended or adjusted under 35 U.S.C. 154(b) by 48 days.

(21) Appl. No.: 11/337,247

(22) Filed: Jan. 19, 2006

(65) Prior Publication Data

US 2006/0121079 A1  Jun. 8, 2006

Related U.S. Application Data

(63) Continuation-in-part of application No. 10/477,914, filed as application No. PCT/DK02/00344 on May 23, 2002, now abandoned.

(30) Foreign Application Priority Data

May 25, 2001 (DK) .................... 2001 00840

(51) Int. Cl.
*A61K 33/38* (2006.01)
*A61K 33/24* (2006.01)
*A61F 13/00* (2006.01)

(52) U.S. Cl. .................. 424/649; 424/618; 424/422

(58) Field of Classification Search ............... 424/649, 424/618, 422
See application file for complete search history.

(56) References Cited

U.S. PATENT DOCUMENTS

| | | | |
|---|---|---|---|
| 2,111,912 A | 3/1938 | Govett .................. 167/91 |
| 3,877,461 A | 4/1975 | Bucalo .................. 128/1 R |
| 4,405,311 A | 9/1983 | Greatbatch ............ 604/20 |
| 4,606,354 A | 8/1986 | Jacob .................... 128/784 |
| 4,634,383 A | 1/1987 | Beyer et al. ........... 433/226 |
| 4,952,150 A | 8/1990 | Schiwiora et al. ..... 433/220 |
| 4,963,184 A | 10/1990 | Diehl et al. ........... 75/247 |
| 4,973,320 A * | 11/1990 | Brenner et al. ........ 604/265 |
| 5,094,689 A | 3/1992 | Stuemke et al. ....... 106/35 |
| 5,204,239 A * | 4/1993 | Gitler et al. ........... 435/7.1 |
| 5,217,594 A | 6/1993 | Henkens et al. ....... 204/403 |
| 5,587,168 A | 12/1996 | Vanonou ............... 424/401 |
| 5,711,314 A | 1/1998 | Ardito ................... 128/885 |
| 5,824,042 A | 10/1998 | Lombardi et al. ..... 623/1 |
| 5,873,904 A * | 2/1999 | Ragheb et al. ......... 623/1.13 |
| 5,889,042 A * | 3/1999 | MacLean et al. ...... 514/427 |
| 5,897,486 A | 4/1999 | Ball et al. .............. 600/25 |
| 6,268,522 B1 | 7/2001 | Hagemeyer et al. ... 560/245 |
| 6,451,003 B1 * | 9/2002 | Prosl et al. ............ 604/507 |
| 2004/0151938 A1* | 8/2004 | Danscher ............... 428/545 |

FOREIGN PATENT DOCUMENTS

| | | |
|---|---|---|
| DE | 196 25 560 A1 | 1/1998 |
| JP | 02-285005 | 11/1990 |
| JP | 04-360667 | 12/1992 |
| JP | 08-089788 | 4/1996 |
| JP | 08-092069 | 4/1996 |
| WO | WO 89/01764 | 3/1989 |
| WO | WO 94/21288 | 9/1994 |
| WO | WO 97/04313 | 2/1997 |

OTHER PUBLICATIONS

Valko et al, Current Medicinal Chemistry, 2005.*
Zhang et al., Current Opinion in Chemical Biology, 2003.*
McKeage et al., Coordination Chemistry Reviews, 2002.*
Henricl, Nature, 1891, p. 345-346.*
Penneys, J. Am. Acad. Dermatol., 1979, 1, 315-320.*
Qasim, Clin. Exp. Immunol, 1997, 108, 438-445.*
Merchant, Biologicals, 1998, 26, 49-59.*
Lewis, Progress in Medicinal Chemistry, 1982, 19, 1-58.*
Turco, Remington's Pharmaceutical Sciences, 1990, ed. Gennaro et al., Chapter 85, pp. 1570-1580.*
Floyd et al.,1996, Chapter 7: Injectable Emulsions and Suspension, in Pharmacueitcal Dosage Forms: Disperse Systems, vol. 2, 2nd ed., H.A. Lieberman et al., eds., p. 288-301.*
Webster's New Collegiate Dictionary, 1977, p. 221,"colloid".
G. Danscher, "In Vivo Liberation Of Gold Ions From Gold Implants. Autometallographic Tracing Of Gold In Cells Adjacent To Metallic Gold", Histochem Cell Biol., vol. 117, pp. 447-452 (2002).

* cited by examiner

*Primary Examiner*—Johann R Richter
*Assistant Examiner*—Abigail Fisher
(74) *Attorney, Agent, or Firm*—Winston & Strawn LLP

(57) ABSTRACT

A method of treatment of a diseased patient in which a dose of at least one heavy metal is delivered to the patient, with a surface area which is accessible for direct contact with the patient's tissue and effects release of heavy metal ions for uptake by immuno reactive cells. The criteria to be complied with in order for the heavy metal to be effective is that the surface area is greater than the surface area of a solid sphere of the same at least one heavy metal, and that the solid sphere and dose have the same weight. In a preferred embodiment, the dose of heavy metals is delivered to the patient as very small hollow particles.

24 Claims, 2 Drawing Sheets

MEDICAMENT AND METHOD OF TREATMENT OF PATIENTS WITH HEAVY METALS

CROSS-REFERENCE TO RELATED APPLICATIONS

Figure 1:
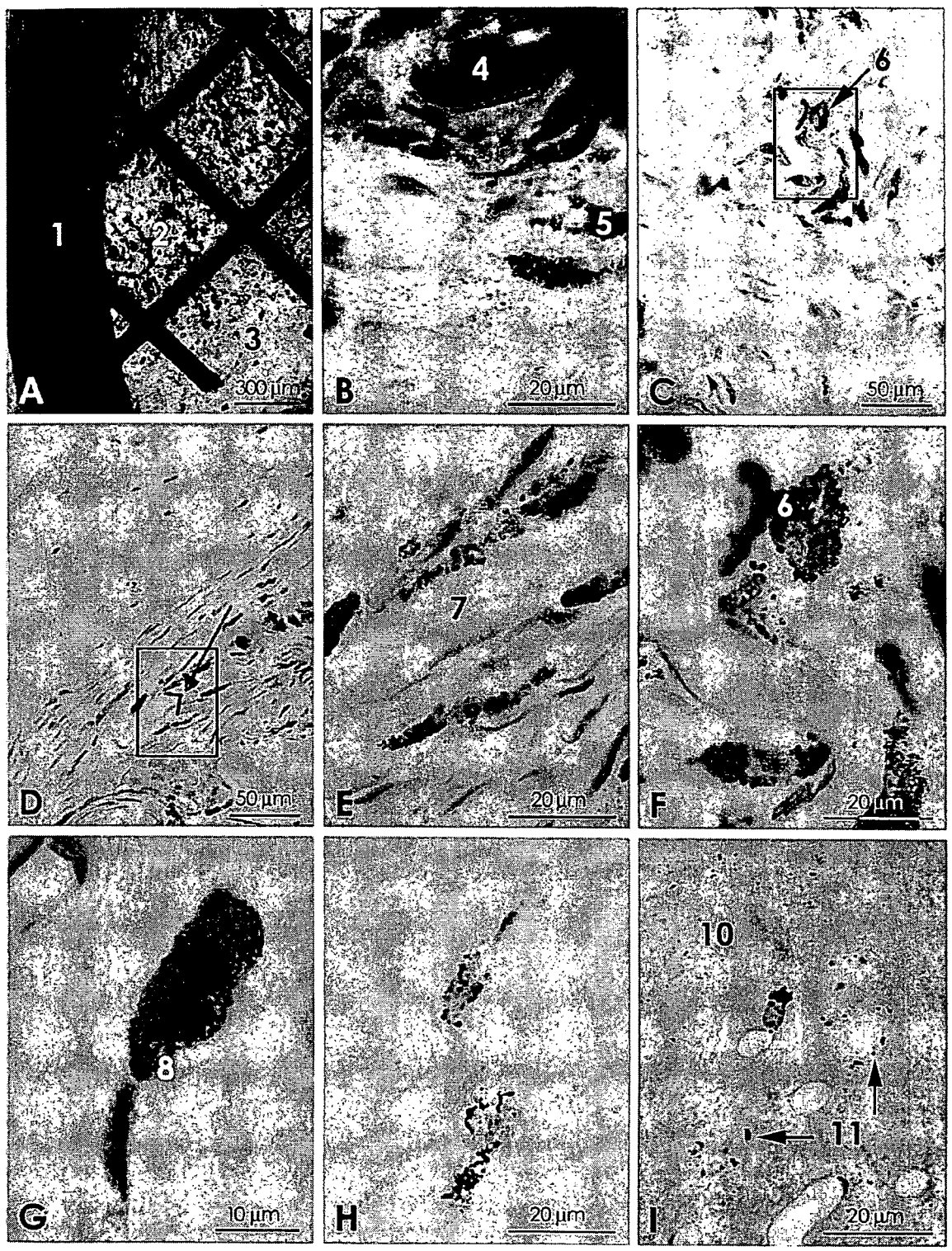

This application is a continuation-in-part of application Ser. No. 10/477,914 filed Feb. 13, 2004 now abandoned, which is the U.S. national phase application of International application PCT/DK02/00344 filed May 23, 2002, the entire content of each of which is expressly incorporated herein by reference thereto.

BACKGROUND

The present invention relates to methods of treatment of a diseased patient in which a dose of at least one heavy metal such as a noble metal, e.g. gold, is delivered to a patient.

In the present application the term "patient" covers all kinds of "mammals" defined as warm-blooded higher vertebrates that nourish their young with milk secreted by mammary glands. In particular, this definition includes humans and other animals that are capable of producing an immune response.

When used in the present application the term "heavy metal" refers to heavy metals as defined by the United Nations Economic Commission for Europe Heavy Metals Protocol: " . . . those metals or, in some cases, metalloids which are stable and have a density greater than 4.5 g/cm$^3$ and their compounds". However, for use in the present application metalloids are not contemplated and therefore not included.

The term "reticulated heavy metal" is in the present invention used for a heavy metal surface delicately wrinkled.

Heavy metals such as the noble metals gold and silver, and mercury have been used since ancient times as cures for a wide range of diseases including tuberculosis, but only within the last 50 years, a more rational basis for the therapeutic use of gold and silver has emerged. The use of gold implants originates from acupuncture where gold needles seem to have been used quite often. In the early 1970s some US veterinarians started to treat dogs suffering from hip dysplasia with gold implants, and since then several veterinary surgeons and medical doctors have implemented the technique on their patients. The authorized and scientifically well-founded use of gold in rheumatoid arthritis is mainly performed with various gold-thio compounds such as gold sodium thiomalate, commercially available from Aventis Pharma as MYO-CRISIN®.

Quite early on it was suggested that gold inhibits the lysosomal enzymes of phagocytotic cells in the inflamed synovial tissue. Although knowledge of the effect of gold ions on the cellular immune response is still relatively sparse, it is recognized that gold ions are powerful inhibitors of macrophages and polymorphonuclear leucocytes, and the ability of gold-thio compounds to suppress inflammation in rheumatic joints was established a long time ago. Gold ions are believed to inhibit antigen processing and to suppress NF-kappa B binding activity and 1-kappa B-kinase activation, resulting in a reduced production of proinflammatory cytokines.

Conventional gold therapy uses rather large doses i.e. the amount of released gold ions are high and involve the whole organism. As gold ions are toxic to the kidneys treatment with gold compounds take place only at hospitals. There are evidence suggesting that very low doses of gold can have pharmacological effects. [Gold And Its Relationship To Neurological/Glandular Conditions; Douglas G. Richards, Ph.D., David L. McMillin, M.A., Eric A. Mein, M.D., Carl D. Nelson, D.C., Intern. J. Neuroscience, 2002, Vol. 112, pages 31-53]. Gold drugs used in rheumatoid arthritis are typically administered in relatively large doses and the relationship between dosage and response is not simple. Dosages as low as 10 mg/week appear according to prior art to be no different from 50 mg/week, which in turn is as effective as 150 mg/week [Speight T M, Holford N H G, (editors). Avery's Drug treatment. 4th edition. Auckland: Adis; 1997: p. 1129].

Kidney damage after treatment with gold compounds is often a typical complication. No prior evidence exists of how little a dose of a gold compounds that can still produce a therapeutic effect. Nor does the prior art discloses unambiguously in which geometrical shape pure heavy metals, such as metallic gold, are optimum applied and delivered to a patient for treatment of diseases and maladies to achieve therapeutic effects.

U.S. Pat. No. 4,606,354 discloses an implant for treatment of arthritic related pain. A carbon fiber coated with a discontinuous gold plating constitutes a self-contained, body-demanded galvanic couples that uses the body joint fluids as an electrical conductive electrolyte. This implant delivers gold ions in a very confined area and the continuous effect relies entirely upon a postulated galvanic action between gold and carbon in combination with the presence of sufficient amounts of body fluids. Another implant for treating rheumatoid arthritis is known from U.S. Pat. No. 4,405,311. Electrically generated gold ions are injected in the patient's joint. This implant needs to be constantly powered by an external battery. Also, U.S. Pat. No. 3,877,461 describes a contraceptive vas deferens valve implant using a.o. a cobber coating as a spermicidal agent and a gold taping wire purely serving as an ingrowth means.

In the method according to WO 94/21288, a composition comprising a colloidal metal in combination with a substance which normally is toxic to a human and an animal capable of producing an immune response is administered to the human or animal. The colloidal metal is added solely to make the toxic substance less toxic or non-toxic to the recipient. WO 94/21288 is however silent about the use of delivering pure metallic gold to the patient. The colloidal metal suggested in WO 94/21288 is HAuCl$_4$. However hydrogen tetrachloroaurate is not a colloidal metal as such but the chemical precursor in the general methods for producing colloidal gold, in which gold nanoparticles are produced in a liquid by reduction of HAuCl$_4$.

Autometallographic (AMG) silver enhancement has been implemented as a tool for enhancing colloidal gold particles bound to antibodies and enzymes. [Danscher, G. (1981) Localization of gold in biological tissue. A photochemical method for light and electronmicroscopy. Histochemistry 71: 81-88; Danscher, G. and J. O. R. Nørgaard (1983) J. Histochem. Cytochem. 31/12: 1394-1398. Holgate et al. (1983) J. of Histochem. Cytochem. 31/7, 938-944]. As is clear from the above the prior art has recognized some advantages of gold treatments but still struggles with the problem of delivering a correct dose and form of heavy metals, in particular gold, to the patient in order to suppress the immuno reactive cells. To obtain suppression of the immuno reactive cells and at the same time avoid or minimize manifestation of undesirable effects it is essential that the correct dose of heavy metal is delivered in a manner and amount appropriate and sufficient for a diseased patient. The present invention now addresses the shortcomings of the prior art in a novel and unexpected way.

SUMMARY OF THE INVENTION

In a first aspect, the present invention provides a reliable and simple method for treatment of a patient for diseases and maladies with implanted heavy metals. The diseases to be treated are those that are responsive to treatment by heavy metals such as gold or silver.

In a second aspect, the present invention provides a reliable and simple method for treatment of a patient for diseases and maladies with locally applied heavy metals.

In a third aspect the present invention provides a method for treatment of a patient for diseases and maladies in which gold ions released from a dose of heavy metals delivered to the patient migrates through the patients tissue and is taken up by immune reactive cells.

In a fourth aspect the invention provides a method in which heavy metals, e.g. gold particles, are applied to internal and/or external surfaces of the patient, subjected to immune reactive reactions with the purpose of damping the immune reaction and suppress pain.

To provide these advantages, the invention provides methods of treatment of a diseased patient in which a dose of at least one heavy metal such as a noble metal, e.g. gold, is delivered to a patient in need of such treatment. Advantageously, the dose has a surface area which is accessible for direct contact with the patient's tissue and effects release of heavy metal ions for uptake by immuno reactive cells. Also, the surface area is greater than the surface area of a solid sphere of the same at least one heavy metal, and the solid sphere and the dose have the same total weight. In other words, within the scope of the present invention, the total weight of the delivered dose is the same as the total weight of a solid sphere of the same material but it exposes a substantially enlarged surface area to the patient's tissue.

A dose of at least one heavy metal, such as gold, satisfying these criteria will expose a surface area from which heavy metal ions are released locally by oxidative liberation provided by phagocytotic cells at desired level and amount which according to the present invention has been established as required and sufficient to stimulate a reaction from the immune system without the use of activation of any external factors, precursors or reactions. For example, the released gold ions exert their inhibitory effect on inflammation either directly by altering chemistry and morphology of peptides and proteins. If the heavy metals ions, such as $Au^+$ and $Au(CN)^-_2$, are in excess they drift further into the intercellular space, and are taken up by mast cells, macrophages and other cells. Finally, the heavy metal, in particular gold containing molecules, accumulates in the lysosomes. After reduction of the tissue sections e.g. with UV-light, the resulting nanocrystals of heavy metal atoms can be visualized by Autometallography (AMG) as described above. Conversely, if the surface area of the dose of a given weight of heavy metal is too small the above-mentioned reactions and effects does not take place to an extent in which treatment of the disease is achieved.

The present invention demonstrates that the larger the surface of gold implants not only releases more gold ions, but also enables such ions to travel farther away from the application site of the implanted dose of heavy metal. Thus, many nearby cells are loaded with e.g. gold ions. As a result of the enlarged surface, the gold influences a much larger area using the smallest possible weight of gold. It has also been found that it is gold ions released from pure gold by cells e.g., upon in vivo tissue contact, provide the desired therapeutic effect and that the method according to the present invention is effective without involvement of any external factors, precursor or reactions.

BRIEF DESCRIPTION OF THE DRAWING FIGURES

The invention will be illustrated more fully below with reference to the drawing, in which FIG. 1, pictures A-I show micrographs of autometallographically (AMG) developed tissue sections, from tissue samples taken near a gold implant, while FIG. 2, pictures A-D show electron micrographs from gold-implanted rat brain.

DETAILED DESCRIPTION OF THE PREFERRED EMBODIMENTS

In preferred embodiments, the surface area of the dose of heavy metal as defined above is at least 5 times greater, in particular at least 10 times greater and especially at least 100 times greater than the surface area of the solid sphere. One way to provide the dose of heavy metal with the inventive surface area is to provide the surface area of the dose of heavy metal with an uneven texture, e.g. texture such as a Rya rug.

In contrast to the prior art disclosures, the dose of the at least one heavy metal is preferably delivered to the patient as solid metallic heavy metal with the above-mentioned enlarged surface area. Such solid, metallic heavy metal can be in the form of solid or hollow particles. If the particles are hollow a considerable surface area for contact with surrounding tissue can be obtained with a low weight dose of heavy metal. Various methods, geometrical shapes and morphologies that provide enhanced surface area of the dose of solid heavy metals to be delivered to the patient are suggested within the scope of the present invention. As examples can be mentioned that the dose of solid heavy metal can be delivered to the patient as coiled up heavy metal networks, reticulated heavy metal, foamed heavy metal, foiled heavy metal, heavy metal webs, or coiled up threads having a diameter of less than 1 mm or combinations of these. The threads may be wound as spring like coils with one or more windings.

The at least one heavy metal can also be an alloy. In one embodiment according to the invention the alloy is a gold-silver alloy applied as micron-sized metal particles in creams to an internal or external surface of the patient. The alloy will at the same time suppress the immune response and suppress microbial growth. In another embodiment the alloy could be a gold-zinc-silver alloy that apart from suppressing the immune response and killing bacteria also enhance healing of wounds.

Any heavy metal having a density of above 4.5 $g/cm^3$ is deemed to be suitable for this invention, with preferred metals and alloys disclosed herein. In the most preferred embodiment according to the present invention the at least one heavy metal can be a noble metal, preferably gold.

Various applications of the most preferred heavy metal, gold, are possible in the method according to the present invention. For example, gold can be distributed as an open (e.g. provided as discontinuous coating) or closed (e.g. provided as continuous coating) gilding on a support medium, such as a prosthesis, or as a layer of gold containing alloy on the bone contacting part of the prosthesis. The use of gilded artificial joints will reduce inflammation and pain and extend the period of time where the prosthesis is firmly placed in the bone i.e., a direct bone-prosthesis contact.

A very large surface area of the dose of gold, or any other heavy metal, is also achieved if the dose is in the form of micron-sized particles having at least one cross-section no less than about 20 microns (μm). Such small particles are easy to distribute at the application site by e.g. injection, spreading, spraying or pouring. Because the released heavy metal ions, e.g. the gold ions, suppresses the immune response the particles will stay where they are delivered. Furthermore, contact with tissue is rapid, easy and to a great extent and as a result release of gold ions correspondingly effective. Therefore, the treatment begins almost immediately after the application of the method according to the present invention.

One preferred method for making the surface area of the dose of at least one heavy metal accessible to the patient is by implantation e.g. injection. Another preferred method is by application of the dose of at least one heavy metal to an internal or external surface of the patient. As an example of an external surface can be mentioned the human skin, and as examples of internal surfaces can be mentioned epithelial surfaces in the lungs and gastro-intestinal canal. For application on internal or external surfaces a dose of the at least one heavy metal particles can be admixed into a solution or carrier substances to be dispensed as drops, aerosols, ointments, lotions, creams, capsules or tablets, if desired. Implantation of a dose of gold particles can be made by injection of the particles close to or directly into a rheumatoid joints.

The treatment method according to the present invention is applicable for treatment of various diseases a.o. autoimmune inflammation or non-microbial inflammation of the skin, such as psoriasis or allergic skin inflammations, in which case the dose of a noble metal is delivered to the human skin admixed or dispersed in a lotion or cream. The method reduces the intensity of the inflammation and eczemas using e.g. 20 micron-sized gold particles can be dispensed or dispersed in creams, ointments or the like. In case the disease is or relates to autoimmune conjunctivitis or a non-microbial conjunctivitis the method can be applied using eye drops to deliver the heavy metal.

The method is also applicable for treatment of a patient for inflammation in the central nervous system by injecting the dose of the at least one heavy metal particles, e.g. gold, into the cerebrospinal fluid or directly into the central nervous system. In such cases the gold particles preferably are hollow and each particle has at least one cross-section of from 20 microns (μm) and e.g. up to 100-300 micron (μm).

In case the disease is or relates to autoimmune maladies in the respiratory system or in the gastro-intestinal canal the method can be applied using aerosol, spray device or inhalers to deliver the heavy metal e.g. in the form of micron-sized gold particles. A nose spray can be used for treatment of allergic reactions in or via the nose.

In case the disease is or relates to an inflammatory condition e.g. in the gastro-intestinal canal, including the mouth, the method can be applied using tablets to be released in the gastro-intestinal canal for suppressing inflammation. For example, micron-sized gold particles can be admixed with a tablet carrier substance and delivered to downgrade the immune response at location in the gastrointestinal canal.

The invention also relates to a medicament for treatment of diseases in a patient; the medicament comprises a dose of particles of at least one heavy metal, wherein the particles have at least one cross-section greater than 20 μm. Only if the particles have this minimum cross-section release of heavy metal ions takes place.

The inventor has demonstrated that gold particles sized less than 20 microns are phagocytosed by the macrophages without effecting release of ions, while particles more than 20 microns cannot be phagocytized but are attached by the macrophages that causes liberation of gold ions form the surfaces of the gold particles. These gold ions are then taken up by the macrophages and can be visualized in the cells at light and electron microscopical levels by Autometallography (AMG).

As noted, it is preferred that the heavy metal used for the medicament is gold or a gold alloy, and that the particles are dispersed in a carrier substance at a distance of between 200-600 μm, preferably between 300-500 μm, especially between 350-450 μm. The particles are delivered to the patient using the method according to the present invention. For example the medicament is delivered to the patient by injection into or close an organ or a joint, or applied to an internal or external immunoresponding surface.

In FIG. 1, pictures A-H show a 5-μm methacrylate embedded connective tissue section, while Picture I shows an Epon embedded 3-μm thick brain section. All sections were counterstained with toluidine blue. In picture A, it will be seen that part of a gold grid 1 dominates the picture. In the closed mesh windows cells are loaded with silver-enhanced gold clusters 2. In the open window far less cells are stained, see numeral 3. In picture B, part of a gold grid mesh is seen at 4 in the upper part of the picture. The dusty appearance of the tissue close to the gold implant represents gold clusters located outside cells. The two loaded cells, cf. 5 further away, are believed to be macrophages. Picture C shows a rather intense AMG staining of macrophages, mast cells and fibroblasts in the connective tissue from subcutis. The gold containing cells, cf. the numeral 6, was located only a few mm from a gold implant. Picture D was taken from an AMG stained section of a demineralised piece of the skull bone. The gold implant was placed in a drifted hole in the skull where it became gradually embedded in the bone. Newly created bone lamella, cf. numeral 7, encircled the connective tissue implant connective tissue. Macrophages and fibroblasts loaded with AMG grains are visible in the connective tissue. Picture E shows a greater magnification of the square than in fig. D, and picture F a greater magnification of the square in C. Picture G shows a photomicrograph of mast cells from gold implanted subcutis. It is noted that only part of the mast cell granules contained gold that is indicated by numeral 8. Picture H shows a typical fibroblast from connective tissue surrounding a gold implant for six weeks. Picture I is taken from a rat neocortex. The implant was located approximately 1 mm, cf. numeral 10, from the AMG stained astrocytes and neurons.

Figure 2:
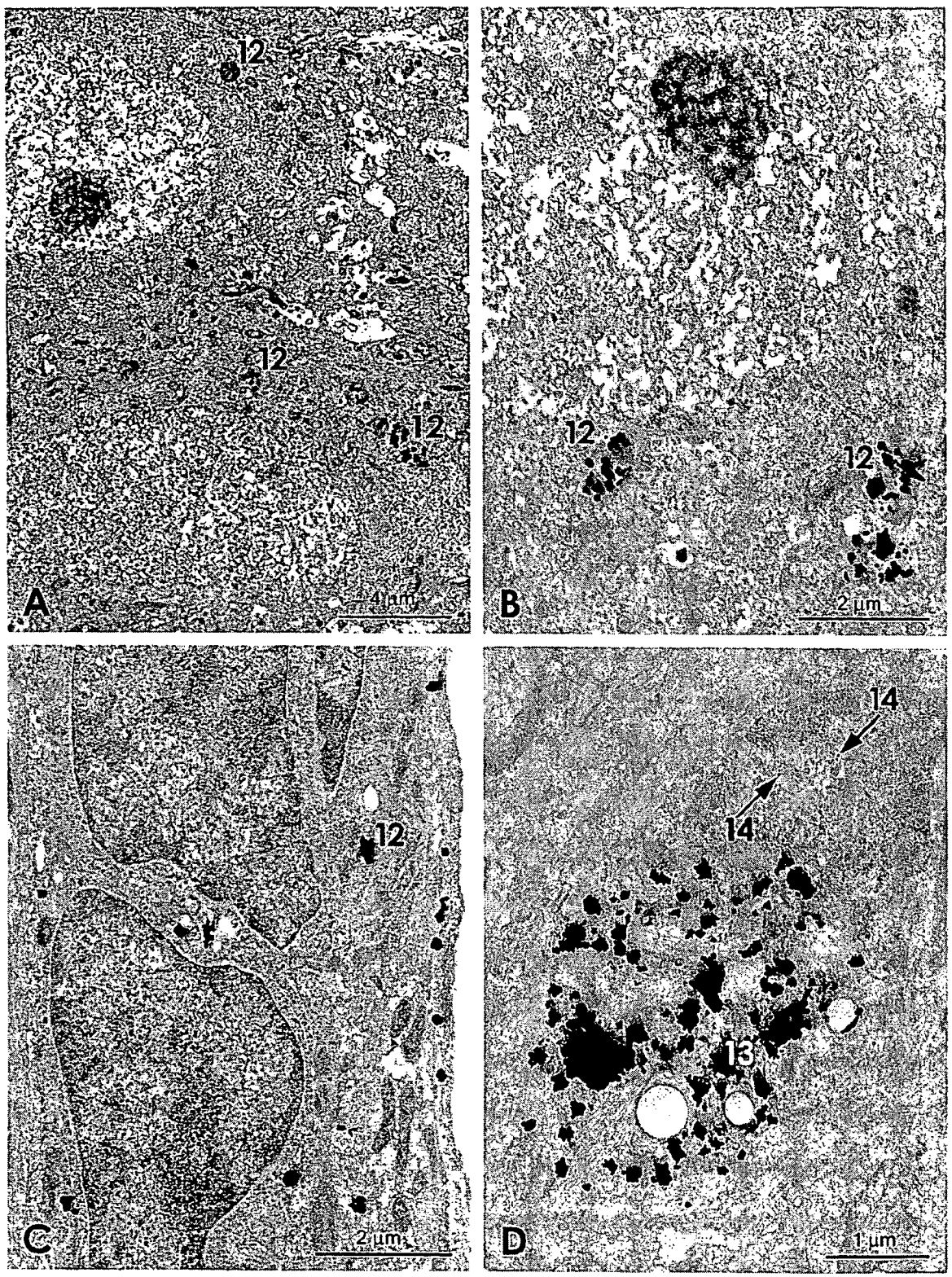

In FIG. 2, picture A shows two minor interneurons from neocortex. Note the exclusive localization of gold in lysosome-like organelles, cf. numeral 12 in FIG. 2, picture A to C. The gold grid based implant was located approximately 1.5 mm from the stained neurons. Picture B shows gold-loaded neuron from caudate putamen. Picture C shows astrocytes adjacent to a capillary (c). Picture D shows astrocytes loaded with gold. The AMG grains seem to be free in the cytoplasm, and the nucleus reveals tiny AMG particles in the euchromatine, cf. the arrows having numeral 14.

EXAMPLES

In the following experiments carried out by the inventor will be explained:

Experiment 1

Twenty-seven adult rats had threads of pure gold implanted in the body. The compact threads were 1.25 mm long and 0.5 mm thick, and weighed approximately 5.5 mg. They were cut from a twenty-four carat gold thread. The gold threads were implanted close to arthritic joints in an attempt to decrease pain and inflammation.

Another ten rats had implanted coiled-up gold grids with a diameter of 3.0 mm and weighing 0.5 mg. The animals were anaesthetized with Nembutal, and the gold threads were implanted by a needle and a stiletto into different parts of the body including the brain close to joints.

At different intervals of survival (10 days to 3 months) the animals were reanaesthetized and transcardially perfused with 3% glutaraldehyde in a 0.1M phosphate buffer. The tissues holding the gold threads or grids were excised and placed in the fixative for at least two hours. The tissue blocks were then either frozen on a stage and cut into 20 µm sections in a cryostat, or they were cut into 100 µm sections in a vibratome.

Every second glass slide was radiated for 30 min with UV light (wavelength 365 nm) upon which all specimens were AMG developed floating in the AMG developer. From the developed vibratome sections, areas of interest were cut out with razor blade and treated with 0.5% osmium tetraoxide for 30 minutes, rinsed, dehydrated and embedded in Epon. Some of the tissue blocks were not fixed in osmium, but directly embedded in methacrylate.

Every second glass slide with cryostat or methacrylate sections was radiated with UV light for 30 min. and placed in a jar, covered by the AMG developer and placed in a 26° C. water bath.

A light-tight hood covered the set-up through the 60 minutes of development. The AMG developer was then replaced by a 5% thiosulphate solution for 10 min in order to remove all silver ions from the sections, and ultimately the sections were rinsed several times in distilled water and counterstained with toluidine blue (15). Semi-thin sections were cut from the Epon blocks and placed on glass slides. They were counterstained with toluidine blue (1%) and analyzed in the light microscope. When photos had been taken, selected sections were reembedded with a drop of Epon on top of a blank Epon. Ultra-thin sections were cut, stained with uranyl and lead, and analysed in an electron microscope.

Controls included sections from tissues not adjacent to gold implants and sections treated with a 10% potassium cyanide solution for 30 min. Blocks of the tissue surrounding the implants were analyzed with Proton Induced X-ray Emission spectroscopy (PIXE). The 20-µm thick cryostat sections were placed on framed micropore polystyrene membranes so thin that the energy loss due to small angle scattering was negligible.

This experiment shows that connective tissue blocks from skin and joints contained a rim of gold ion-imbibed tissue around the gold implants, cf. also FIG. 1, pictures A and B. In this juxta-positioned implant tissue, macrophages and mast cell were the first to show accumulation of gold, cf. FIG. 1, pictures B-H. Already after 14 days the first traces of AMG enhanced gold clusters could be observed, and after one to two months an increasing amount of loaded cells including fibroblasts were seen. Not all macrophages or mast cells showed an uptake of gold, quite the reverse. Even close to the gold implants some macrophages and mast cells completely void of gold were observed. The most heavily loaded cells, whether macrophages or mast cells, showed signs of degeneration. In cells showing degeneration, EM magnifications showed gold accumulations that were not enclosed by a membrane, but seemed to be located free in the cytoplasm.

The pattern gave the impression that lysosomes/vesicles take up increasing amounts of gold until the enclosing membrane bursts. Cells with free gold accumulations sometimes had gold accumulations in the nucleus. Cells closer to the gold implants were more loaded than cells farther away, and macrophages and mast cells stained more heavily than fibroblasts. Fibroblasts became loaded only after long periods of time, approximately two months in the case of rod-shaped gold threads, but faster if coiled-up gold grids were used as implants.

Also the longer the implant had been in the tissue, the more stained cells and the broader the rim of gold-imbibed tissue. The coiled-up grid implants, having a substantially increased surface compared to the rod-shaped gold threads, released far more gold ions, recorded as a drastic increase in the amount of stained cells and in the staining intensity in the individual cells. Kidneys and livers from implanted animals were examined in order to test whether gold ions spread systematically.

In cases where more than one coiled-up grid was implanted, a faint staining in the proximal tubule of the kidney was recorded in some animals, while the liver was void of AMG grains. If coiled-up grids were implanted directly in the kidney, some release of gold ions could be detected in nearby cells, but of all the implanted tissues those in the kidney caused the least release of gold ions. The compact gold threads implanted in the brain revealed a tiny rim of imbibed cells closely associated to the implant, but gold ion-loaded neurons and glia cells could be traced further from the rim, cf. FIG. 1, picture 1. The coiled-up grid implants resulted in an up to several millimeter wide zone of gold-loaded neurons and glia cells around the implant. Again some neurons and glia cells were completely void of gold. In a few animals the implant had been embedded in connective tissue, and no AMG grains were detected in the surrounding neurons and glia cells.

In both glia cells and neurons gold was found to be located in lysosome-like vesicles, cf. FIG. 2, pictures A-D. The loaded vesicles were spread throughout the neuronal somata and into the major dendrites. Most of the gold-containing glia cells seemed to be protoplasmatic astrocytes, cf. FIG. 2, pictures C and D, but the possibility that oligodendroglia and microglia take up gold cannot be excluded at this early stage. In addition to the fact that AMG staining was observed only in tissues relatively close to the gold implants, several controls were introduced in order to ensure that the staining was caused by gold nanocrystals or nanosized clusters: the tissue sections were treated with 10% aqueous potassium cyanide for 30 minutes. This treatment resulted in a complete removal of the catalyst, and the following AMG development resulted in blank sections. The multi-element analysis of cryostat sections with PIXE showed that the tissue surrounding gold implants contained 38 ppm. gold, while tissue taken 1 cm from gold implant was void of gold (<0.39 p.p.m.).

Experiment 2

The experiments were performed on ten animals using the Animal model "Heterotopic heart transplantation to the neck vessels in rats". The animal model was originally described in 1971 by Heron et al. [Heron I., A technique for accessory cervical heart transplantation in rabbits and rats, Acta Pathol. Microbiol. Scand., [A] 1971; 79(4):366-372] and later a few modifications were added by Lim et al. [Lim S M, Li S Q., Accessory heart graft as a surgical model in studies of transplantation immunology, Ann Acad. Med., Singapore 1991; 20(4):478-483]. It is a well-established surgical model for in vivo studies of transplantation immunology and has been widely used the last 20 years.

100 mg of gold particles as disclosed herein having a surface area that is greater than that of a solid sphere having a weight comparable to a gold particle and at least one cross-section between 40-250 μm were used per operation. The gold particles were poured onto the transplanted heart just before the wound was closed. The animals lived 5 to 6 days before the transplanted heart stopped. When analyzing cross-sections from the transplanted heart surrounded by granulose tissue, it was found that almost all cells on the skin close part of the heart were loaded with released gold ions while on the opposite side of the heart the granulose tissue was completely void of gold accumulations in the cells. It was also observed that the gold treated granulose tissue was distinctly growth inhibited. This was found to be true for all ten animals undergoing transplantation.

Ongoing experiments provide a clear indication confirming the above-mentioned essential relationship between surface area and weight of the dose of delivered heavy metal.

The invention thus demonstrates improvements in treating diseases that respond to the administration or introduction of heavy metals such as gold or silver by providing an enhanced surface area of the heavy metal dose to be administered. This enables a greater amount of heavy metal to be delivered to the patient to increase the efficacy of such treatments, as disclosed herein.

What is claimed is:

1. A method for improving conventional therapy for the treatment of inflammatory diseases using heavy metals, wherein the improvement comprises delivering to a patient in need of such treatment a dose of at least one heavy metal of gold, silver or one of their alloys as heavy metal particles having a cross-sectional diameter of at least 20 μm and having the same weight but a greater surface area than that of solid spheres of the same at least one heavy metal, and wherein the heavy metal in the dose has a configuration, size or shape that provides a surface area for direct contact with the patient's tissue and that facilitates release of heavy metal ions for uptake by macrophages without phagocytosis of the particles.

2. The method of claim 1, wherein the inflammatory diseases are selected from the group consisting of conjunctivitis, rheumatoid arthritis, inflammation of the skin, and inflammation in the central nervous system, respiratory system or gastro-intestinal canal.

3. The method of claim 2, wherein the inflammatory disease is psoriasis, conjunctivitis, or rheumatoid arthritis.

4. The method of claim 1, wherein the disease is conjunctivitis.

5. The method of claim 1, wherein the disease is inflammation in the central nervous system.

6. The method of claim 1, wherein the disease is rheumatoid arthritis.

7. The method of claim 1, wherein the disease is inflammatory conditions in the gastro-intestinal canal.

8. The method of claim 1, wherein the surface area of the particles is at least 5 times greater than the surface areas of solid spheres of the same at least one heavy metal.

9. The method of claim 1, wherein the dose of at least one heavy metal is delivered to the patient as solid heavy metal particles.

10. The method of claim 1, wherein the dose of at least one heavy metal is delivered to the patient as hollow heavy metal particles.

11. The method of claim 1, wherein the heavy metal is gold or a gold alloy and the dose of gold is delivered to the patient as micron-sized gold particles.

12. The method of claim 1, wherein the dose of at least one heavy metal is delivered by implantation into the patient.

13. The method of claim 12, wherein the patient is treated for rheumatoid arthritis and implantation of the dose of heavy metal particles is made by injection of the particles close to or into rheumatoid joints of the patient.

14. The method of claim 1, wherein the dose of at least one heavy metal is made accessible by application on an internal or external surface of the patient.

15. The method of claim 14, wherein the surface is an epithelial surface and the dose of the at least one heavy metal particles is mixed into a solution or carrier substance to be dispensed as drops, aerosols, ointments, lotions, creams, capsules or tablets.

16. The method of claim 15, wherein the patient is treated for inflammation of the skin or psorlasis.

17. The method of claim 1, wherein the patient is treated for inflammation of the central nervous system by injecting the dose of heavy metal particles into the cerebrospinal fluid or directly into the central nervous system.

18. The method of claim 1, wherein the surface area of the particles is at least 10 to 100 times greater than the surface area of solid spheres of the same at least one heavy metal.

19. The method of claim 1, wherein the greater surface area of the heavy metal particles provides greater stimulation and uptake by microphages compared to particles having a lesser surface area and without phagocytosis of the particles.

20. The method of claim 1, wherein the heavy metal is gold or a gold alloy.

21. The method of claim 20, wherein the inflammatory disease is an inflammation of the skin or psorlasis.

22. The method of claim 21, wherein the heavy metal is gold and the inflammatory disease is psoriasis.

23. The method of claim 1, wherein the inflammatory disease is an inflammation of the skin.

24. The method of claim 1, wherein the inflammatory disease is psoriasis.

* * * * *

UNITED STATES PATENT AND TRADEMARK OFFICE
CERTIFICATE OF CORRECTION

PATENT NO.       : 7,655,261 B2                                                      Page 1 of 1
APPLICATION NO. : 11/337247
DATED            : February 2, 2010
INVENTOR(S)      : Danscher It is certified that error appears in the above-identified patent and that said Letters Patent is hereby corrected as shown below:

Title Page:
Item (56) References Cited, U.S. PATENT DOCUMENTS, add the following references:
|  |  |  |  |
| --- | --- | --- | --- |
| 2,953,456 A | 9/1960 | Mohler et al. | 99/14 |
| 3,010,829 A | 11/1961 | Turner | 99/107 |
| 3,256,098 A | 6/1966 | Ohtaki | 99/124 |
| 3,929,890 A | 12/1975 | Pfister | 426/580 |
| 4,113,884 A | 9/1978 | Krasovec et al. | 426/56 |
| 2005/0037109 A1 | 2/2005 | Soerensen et al. | 426/56 |

Item (56) References Cited, FOREIGN PATENT DOCUMENTS, add the following references:
| | | |
| --- | --- | --- |
| EP | 1 163 853 A1 | 12/2001 |
| FR | 2 541 308 | 8/1984 |
| WO | WO 94/01003 | 1/1994 |
| WO | WO 98/17127 | 4/1998 |

Column 10:
Line 30 (claim 16, line 2), change "psorlasis" to -- psoriasis --
Line 45 (claim 21, line 2), change "psorlasis" to -- psoriasis --

Signed and Sealed this

Sixteenth Day of March, 2010

David J. Kappos
*Director of the United States Patent and Trademark Office*